(12) United States Patent
Benje et al.

(10) Patent No.: US 9,849,400 B2
(45) Date of Patent: Dec. 26, 2017

(54) METHOD FOR CONCENTRATING AQUEOUS LYE AND APPARATUS SUITABLE THEREFOR

(75) Inventors: Michael Benje, Bad Soden (DE); Sven Petersen, Dresden (DE); Michael Kleiber, Hattersheim (DE)

(73) Assignees: THYSSENKRUPP UHDE GMBH, Dortmund (DE); VINNOLIT GMBH & CO. KG, Burgkirchen (DE)

( * ) Notice: Subject to any disclaimer, the term of this patent is extended or adjusted under 35 U.S.C. 154(b) by 617 days.

(21) Appl. No.: 14/233,842

(22) PCT Filed: Jun. 27, 2012

(86) PCT No.: PCT/EP2012/002688
§ 371 (c)(1),
(2), (4) Date: Jan. 20, 2014

(87) PCT Pub. No.: WO2013/010621
PCT Pub. Date: Jan. 24, 2013

(65) Prior Publication Data
US 2014/0158518 A1    Jun. 12, 2014

(30) Foreign Application Priority Data
Jul. 21, 2011    (DE) .................. 10 2011 108 211

(51) Int. Cl.
*B01D 1/00*    (2006.01)
*C07C 17/02*    (2006.01)
(Continued)

(52) U.S. Cl.
CPC .......... *B01D 1/0058* (2013.01); *B01D 1/065* (2013.01); *B01D 1/26* (2013.01); *B01D 1/28* (2013.01);
(Continued)

(58) Field of Classification Search
CPC ........ B01D 1/0058; B01D 1/065; B01D 1/26; B01D 1/28; C01D 1/42; C07C 17/02; C07C 19/045
See application file for complete search history.

(56) References Cited

U.S. PATENT DOCUMENTS 3,332,470 A * 7/1967 Chirico .................... B01D 1/26
                                                              159/17.3
4,082,616 A * 4/1978 Antony .................... B01D 1/16
                                                              202/173
(Continued)

FOREIGN PATENT DOCUMENTS

CN    101228105    5/2012
DE    3226042      1/1984
(Continued)

OTHER PUBLICATIONS

Taiwanese Office Action for Application No. 101124284, English translation attached to original, Dated Dec. 30, 2015, All together 13 pages.
(Continued)

*Primary Examiner* — Jonathan Miller
(74) *Attorney, Agent, or Firm* — Brooks Kushman P.C.

(57) ABSTRACT

Method of concentrating aqueous alkali and apparatus suitable for this purpose. A very energy-saving method of concentrating aqueous alkali originating, for example, from a chloralkali electrolysis plant and an apparatus suitable for this purpose are described. The method/the apparatus utilizes heat of reaction from the formation of 1,2-dichloroethane and includes multistage concentration of the aqueous alkali, where at least part of the heat required for concentrating the aqueous alkali originates from the plant for preparing 1,2-dichloroethane and at least a further part of the heat required for concentrating the aqueous alkali originates from at least one of the higher stages of the plant for
(Continued)

concentrating the aqueous alkali and is used for partial heating of the first stage. The apparatus can be used for retrofitting existing integrated plants made up of a DCE plant and chloralkali electrolysis or in the erection of new plants.

19 Claims, 4 Drawing Sheets

(51) Int. Cl.
  *C01D 1/42* (2006.01)
  *B01D 1/26* (2006.01)
  *B01D 1/28* (2006.01)
  *B01D 1/06* (2006.01)

(52) U.S. Cl.
  CPC ............... *C01D 1/42* (2013.01); *C07C 17/02* (2013.01); *Y02P 20/129* (2015.11)

(56) References Cited

U.S. PATENT DOCUMENTS

| | | | | |
|---|---|---|---|---|
| 4,132,588 | A * | 1/1979 | Ogawa | C01D 1/42 159/17.1 |
| 4,263,102 | A * | 4/1981 | Schorr | B01D 1/00 159/17.1 |
| 4,270,974 | A * | 6/1981 | Greenfield | B01D 1/14 159/16.3 |
| 6,132,555 | A * | 10/2000 | Rikkinen | B01D 1/26 159/17.2 |
| 6,191,329 | B1 | 2/2001 | Benje | |
| 6,229,059 | B1 | 5/2001 | Motz | |
| 7,671,243 | B2 * | 3/2010 | Petersen | B01J 19/2425 570/246 |
| 8,742,182 | B2 * | 6/2014 | Petersen | C07C 17/02 570/224 |
| 2009/0082602 | A1 * | 3/2009 | Petersen | C07C 17/02 570/224 |
| 2009/0306439 | A1 | 12/2009 | Petersen et al. | |

FOREIGN PATENT DOCUMENTS

| | | |
|---|---|---|
| DE | 19703857 | 8/1998 |
| DE | 19834083 | 2/2000 |
| DE | 19904836 | 8/2000 |
| DE | 10107092 | 8/2002 |
| DE | 102005030511 | 1/2007 |
| DE | 102005030512 | 1/2007 |
| DE | 102005044177 | 4/2007 |
| EP | 1928810 | 12/2011 |
| EP | 1899287 | 9/2013 |
| WO | 2007031223 | 3/2007 |

OTHER PUBLICATIONS

Feng Sili, Chemical Engineering 1983, pp. 79-84, "The Discussion of the Technique of Improving the Evaporation of Caustic Soda", English translation of document attached to orignal, All together 9 Pages.

Interantional Search Report for PCT/EP2012/002688, English translation attached to original, Both completed by the European Patent Office on Oct. 12, 2012, All together 5 Pages.

* cited by examiner

METHOD FOR CONCENTRATING AQUEOUS LYE AND APPARATUS SUITABLE THEREFOR

CROSS-REFERENCE TO RELATED APPLICATION

This application is the U.S. national phase of PCT Application No. PCT/EP2012/002688 filed on Jun. 27, 2012, which claims priority to German Patent Application No. 10 2011 108 211.9 filed on Jul. 21, 2011, the disclosures of which are incorporated in their entirety by reference herein.

BACKGROUND OF THE INVENTION

1. Field of the Invention

The invention relates to a method and an apparatus for concentrating aqueous alkali in plants for producing 1,2-dichloroethane.

2. Description of the Related Art 1,2-Dichloroethane, (hereinafter "DCE") is used predominantly as intermediate in the preparation of monomeric vinyl chloride which is in turn used as intermediate for the preparation of polyvinyl chloride. The reaction of DCE to form monomeric vinyl chloride forms hydrogen chloride HCl. This is preferably used in the preparation of DCE by oxychlorination of ethene by means of HCl and oxygen. An alternative route for preparing DCE proceeds via the direct chlorination of ethene by means of chlorine. In the industrial preparation of DCE, both routes are employed, so that there is a balance between the hydrogen chloride produced and that which is consumed, according to the following reaction equations:

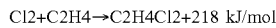

$Cl_2 + C_2H_4 \rightarrow C_2H_4Cl_2 + 218$ kJ/mol

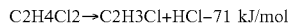

$C_2H_4Cl_2 \rightarrow C_2H_3Cl + HCl - 71$ kJ/mol

$C_2H_4 + 2HCl + \frac{1}{2}O_2 \rightarrow C_2H_4Cl_2 + H_2O + 238$ kJ/mol

The chlorine required for the direct chlorination is frequently produced in a chloralkali electrolysis plant located in the vicinity of the DCE plant. As is known, sodium hydroxide solution is also formed here, typically in a concentration of about 30% by weight.

This alkali represents a material of value but has to be concentrated for economic reasons. Modern chloralkali electrolysis plants are equipped with a concentration unit for the alkali obtained. This unit is typically operated by means of steam and typically produces alkalis having a concentration of 50% by weight or more of sodium hydroxide. The amount of steam required for operating the concentration unit represents a not inconsiderable part of the operating costs of the chloralkali electrolysis plant.

It has already been proposed that heat from the DCE process be used for evaporating or concentrating sodium hydroxide solution from the chloralkali electrolysis. DE 10 2005 044 177 A1 describes a method and an apparatus for utilizing the heat of condensation obtained in the purification of DCE from a direct chlorination plant. Here, the heat of condensation of the vapor obtained in the purification of DCE by distillation is at least partly used for evaporation of the sodium hydroxide solution originating from a chloralkali electrolysis plant. DE 10 2005 030 511 A1 and DE 10 2005 030 512 A1 describe a method and apparatuses for utilizing the heat of reaction arising in the preparation of DCE. Here, the heat of reaction from a direct chlorination plant is at least partly used for evaporation of the sodium hydroxide solution originating from a chloralkali electrolysis plant. Apparatuses which comprise a shell-and-tube heat exchanger having two fixed tube plates and an NaOH bottom part and are configured so that sodium hydroxide solution is conveyed inside the tubes and DCE is conveyed along the outside of the tubes and have devices for introducing sodium hydroxide solution into the interior of the tubes and distributing it over them are used.

These previously known methods and apparatuses allow very efficient operation of the process. For the purposes of process optimization, further process improvements are sought and the process should be able to be operated in an even more resource-conserving manner.

SUMMARY OF THE INVENTION

It is an object of the present invention to provide a method and a suitable corresponding apparatus for concentrating aqueous alkali, with this method and apparatus allowing a more energy-efficient work-up compared to known methods and apparatuses. In addition, the apparatus should be constructed so that it can be retrofitted in a simple way in existing combinations of DCE plants with chloralkali electrolysis plants.

The present invention provides a method of utilizing the heat of reaction from the formation of 1,2-dichloroethane for concentrating aqueous alkali, wherein the aqueous alkali is concentrated in a plurality of stages, at least part of the heat required for concentrating the aqueous alkali originates from a plant for preparing 1,2-dichloroethane and at least a further part of the heat required for concentrating the aqueous alkali originates from at least one of the higher stages of the plant for concentrating the aqueous alkali and is used for the partial heating of the first stage.

BRIEF DESCRIPTION OF THE DRAWINGS

The invention is illustrated by way of example below with the aid of four figures, without a restriction being intended thereby. The figures show.

DETAILED DESCRIPTION OF THE PREFERRED EMBODIMENTS

Figure 1:
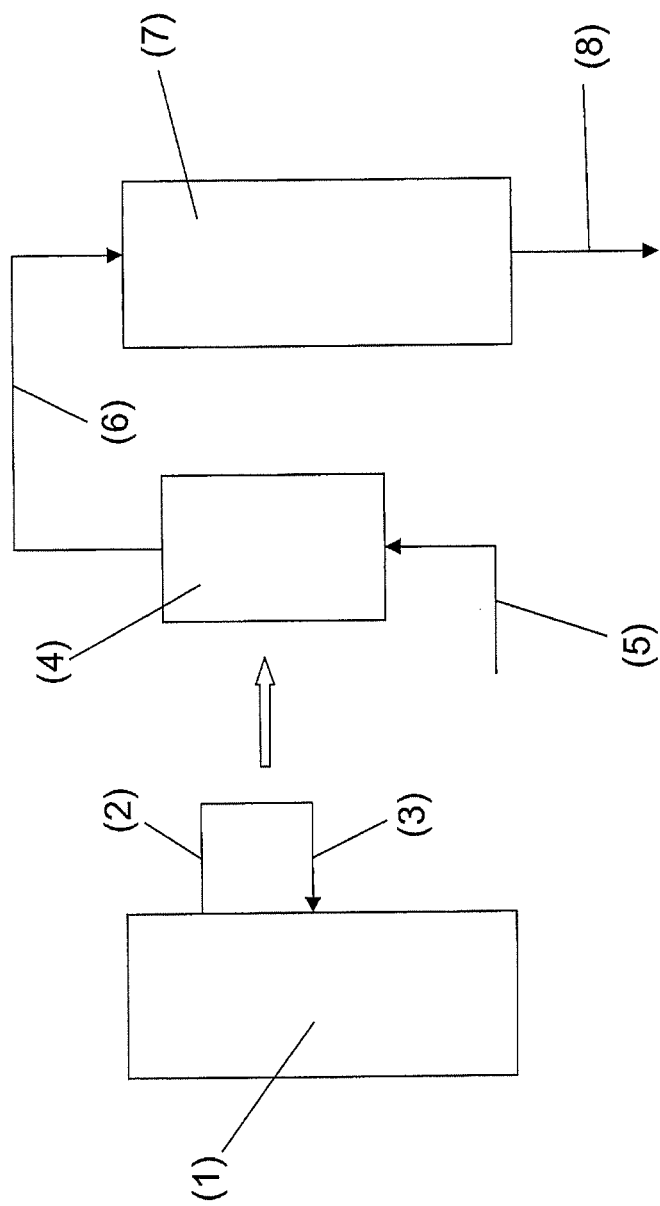
FIG. 1: An in-principle sketch of a plant according to the invention (produced by retrofitting of a conventional plant) and the method of the invention.

For the purposes of this description, aqueous alkali is any alkali which can be concentrated by evaporation of water. The alkali is preferably an aqueous alkali metal hydroxide, very particularly preferably aqueous sodium hydroxide.

This aqueous alkali metal hydroxide typically originates from a chloralkali electrolysis plant, in particular from a chloralkali electrolysis plant present in parallel to the DCE plant. This chloralkali electrolysis plant produces an aqueous alkali which has to be concentrated before being sold as material of value. The concentration of alkali metal hydroxide in an aqueous alkali metal hydroxide originating from a chloralkali electrolysis is typically about 30% by weight. On the other hand, as materials of value aqueous alkali metal hydroxides should have an alkali metal hydroxide content of at least 50% by weight.

Preference is given to a method in which the aqueous alkali used originates from a chloralkali electrolysis plant.

For the purposes of this description, a stage is a process step in which the aqueous alkali is concentrated by evaporation of water.

These stages can be preceded and/or followed by heating steps of the aqueous alkali or the concentrates. Thus, for example, the dilute aqueous alkali used as starting material can firstly be preheated and then concentrated in a first stage in a concentration unit; or the preconcentrated aqueous alkali can be subjected after the first stage after leaving the first concentration unit to a heating step and then be subjected to a further stage in a second concentration unit. Other combinations of concentration steps and heating steps are also possible. The apparatuses used in these steps can be operated using waste heat from the preceding steps. According to the invention, at least part of the waste heat comes from the plant for preparing 1,2-dichloroethane.

The method of the invention can be carried out in two stages or in particular in three stages or even in more than three stages. Particular preference is given to a method operated in three stages.

Preference is given to methods carried out in at least two stages which comprise the following steps:
  i) production of a first aqueous alkali concentrate from a dilute aqueous alkali in a first concentration unit,
  ii) concentration of the first aqueous alkali concentrate to give a second aqueous alkali concentrate in a second concentration unit,
  iii) operation of the second concentration unit at least partially by means of heat originating from a plant for preparing 1,2-dichloroethane and
  iv) operation of the first concentration unit at least partially by means of heat originating from the second concentration unit.

Particular preference is given to two-stage methods in which a heating unit for the first aqueous alkali concentrate is present between first and second concentration units, which preferably comprises from one to three heat exchangers connected in series and is heated by heat originating from the plant for preparing 1,2-dichloroethane and/or is heated by heat originating from the second concentration unit and/or is heated by heat originating from a plant for concentrating aqueous alkali which is combined with a plant for chloralkali electrolysis.

Particular preference is given to three-stage methods comprising the following steps:
  i) production of a first aqueous alkali concentrate from a dilute aqueous alkali in a first concentration unit,
  ii) concentration of the first aqueous alkali concentrate to give a second aqueous alkali concentrate in a second concentration unit,
  iii) concentration of the second aqueous alkali concentrate to give a third aqueous alkali concentrate in a third concentration unit,
  iv) operation of the second and third concentration units at least partially by means of heat originating from a plant for preparing 1,2-dichloroethane and
  v) operation of the first concentration unit at least partially by means of heat originating from the second and third concentration units.

To produce the first aqueous alkali concentrate from aqueous alkali in the first concentration unit, it is possible to use any apparatuses suitable for this purpose. Preference is given to using heat exchangers or evaporators for this purpose.

At least part of the thermal energy required for operating the first concentration unit, for example at least 50%, preferably at least 80%, of the thermal energy required in this unit, originates from the downstream concentration unit(s). This can be thermal energy obtained by use of heat exchangers and/or thermal energy obtained from the compressed steam which has been obtained in operation of the downstream concentration apparatuses.

To produce the second aqueous alkali concentrate from the first aqueous alkali concentrate in the second concentration unit, it is likewise possible to use any apparatuses suitable for this purpose. Preference is given to using falling film evaporators for this purpose; however, it is also possible to use heat exchangers or evaporators of another type. At least part of the thermal energy required for operation of the second concentration unit, for example at least 50%, preferably at least 80%, of the thermal energy required in this unit, is obtained from liquid and/or gaseous DCE originating from the DCE plant. This can be thermal energy obtained by use of heat exchangers from the liquid DCE circulation stream or by condensation of the gaseous DCE, both from the DCE plant.

To produce the third aqueous alkali concentrate from the second aqueous alkali concentrate in the third concentration unit, it is likewise possible to use any apparatuses suitable for this purpose. Preference is here likewise given to using heat exchangers or evaporators. At least part of the thermal energy required for operation of the third concentration unit, for example at least 50%, preferably at least 80%, of the thermal energy required in this unit, is obtained by condensation of gaseous DCE originating from the DCE plant.

In a particularly preferred embodiment of the method of the invention, part of the condensed DCE originating from the third concentration unit is branched off for heating the second concentration unit and combined with the liquid DCE originating from the DCE plant, viz. the DCE circulation stream.

The present invention additionally provides an apparatus for concentrating aqueous alkali, which is coupled with a plant for preparing 1,2-dichloroethane and comprises the following elements:
  A) a first concentration unit for concentrating aqueous alkali and producing a first aqueous alkali concentrate, which is heated by means of waste heat from a second concentration unit, and
  B) a second concentration unit for concentrating the first aqueous alkali concentrate and producing a second aqueous alkali concentrate, which is heated at least partially by means of heat originating from a plant for preparing 1,2-dichloroethane.

Existing DCE plants associated with a chloralkali electrolysis plant can be retrofitted with the apparatus of the invention. This is particularly appropriate when the chloralkali electrolysis plant is already equipped with a unit for concentrating aqueous alkali. Retrofitting with an apparatus according to the invention can be carried out in such a way that the dilute aqueous alkali originating from the chloralkali electrolysis plant is firstly concentrated in the apparatus according to the invention, for example from about 30% by weight to about 40% by weight of alkali metal hydroxide, and then concentrated further in the unit already present in the chloralkali electrolysis plant for concentrating aqueous alkali, for example from about 40% by weight to about at least 50% by weight of alkali metal hydroxide. The heat for operating the apparatus of the invention originates at least partly from the DCE plant. The total energy consumption of this integrated plant can therefore be reduced, since the unit present in the chloralkali electrolysis plant requires a smaller total amount of hot steam for operation than is the case without the use of the apparatus of the invention.

In the case of newly built DCE plants, the installation of an apparatus according to the invention operated in three stages is preferred. When a chlorine electrolysis plant is combined with a DCE plant, the installation of a unit present in the chloralkali electrolysis plant for concentrating aqueous alkali can be dispensed with; this function can be taken over completely by the apparatus according to the invention.

Particularly preferred apparatuses according to the invention additionally comprise, in addition to the above-described elements A) and B), a heating unit C) for the first aqueous alkali concentrate, which is located between the first and second concentration units and preferably comprises from one to three heat exchangers connected in series and is heated by heat originating from the plant for preparing 1,2-dichloroethane and/or is heated by heat originating from the second concentration unit and/or is heated by heat originating from a plant for concentrating aqueous alkali which is combined with a plant for chloralkali electrolysis.

Very particular preference is given to apparatuses having a heating unit C which comprises three heat exchangers connected in series, of which one heat exchanger is heated by heat originating from the plant for preparing 1,2-dichloroethane, a further heat exchanger is heated by heat originating from the second concentration unit and a further heat exchanger is heated by heat originating from a plant for concentrating aqueous alkali which is combined with a plant for chloralkali electrolysis.

Particularly preferred apparatuses according to the invention additionally comprise, in addition to the above-described elements A) and B), the following elements:

D) a third concentration unit for concentrating the second aqueous alkali concentrate, which is operated at least partially by means of heat originating from the plant for preparing 1,2-dichloroethane, and optionally E) a heat exchanger unit for recovering heat from the third concentration unit, which is connected to the second concentration unit in such a way that the recovered heat can be utilized for preheating the first aqueous alkali concentrate upstream of the second concentration unit.

Preference is given to apparatuses in which the first concentration unit is heated by means of steam from a steam compression unit which compresses steam originating from the second concentration unit and optionally from further concentration units.

Preference is given to apparatuses in which the first concentration unit and the third concentration unit are each one or more heat exchangers or evaporators connected in series and in which the second concentration unit is a falling film evaporator.

Preference is given to apparatuses in which the first concentration unit and the third concentration unit are formed by one or more plate heat exchangers.

The apparatus of the invention allows particularly energy-saving operation of a concentration apparatus for aqueous alkali with a simultaneously high efficiency of enrichment.

FIG. 1 describes the principle of the method of the invention/the apparatus of the invention for the example of retrofitting of an existing plant.

FIG. 1 depicts a DCE plant (here a direct chlorination plant) (1). DCE vapor (2) is branched off from this and heat is recovered by condensation. The DCE condensate (3) is recirculated to the DCE plant (1). The heat obtained is used for heating a multistage concentration apparatus (4) for aqueous alkali. In the example shown, aqueous sodium hydroxide (5) having a concentration of about 30% by weight is introduced into the multistage concentration apparatus (4). The aqueous sodium hydroxide originates from a chloralkali electrolysis plant (not shown) which is equipped with a conventional concentration apparatus (7) for aqueous alkali. This is operated using hot steam (not shown). In the multistage concentration apparatus (4), the aqueous sodium hydroxide (5) is concentrated by evaporation of water and leaves this apparatus (4) as preconcentrated aqueous sodium hydroxide (6) having a concentration of about 40% by weight. This preconcentrated aqueous sodium hydroxide (6) is then introduced into the conventional concentration apparatus (7) where the preconcentrated aqueous sodium hydroxide (6) is concentrated further by evaporation of further water and leaves the apparatus (7) as aqueous sodium hydroxide (8) having a concentration of 50% by weight or more. Not shown in this in-principle sketch is that part of the heat required for heating the multistage concentration apparatus (4) originates from waste heat originating from the conventional concentration apparatus (7). Integrated plants which are made up of existing DCE plants and chloralkali electrolysis plants and already contain a conventional concentration apparatus (7) can be retrofitted with the multistage concentration apparatus (4) shown in FIG. 1. For this purpose, the multistage concentration apparatus (4) is connected as described above to the existing plants.

Figure 2:
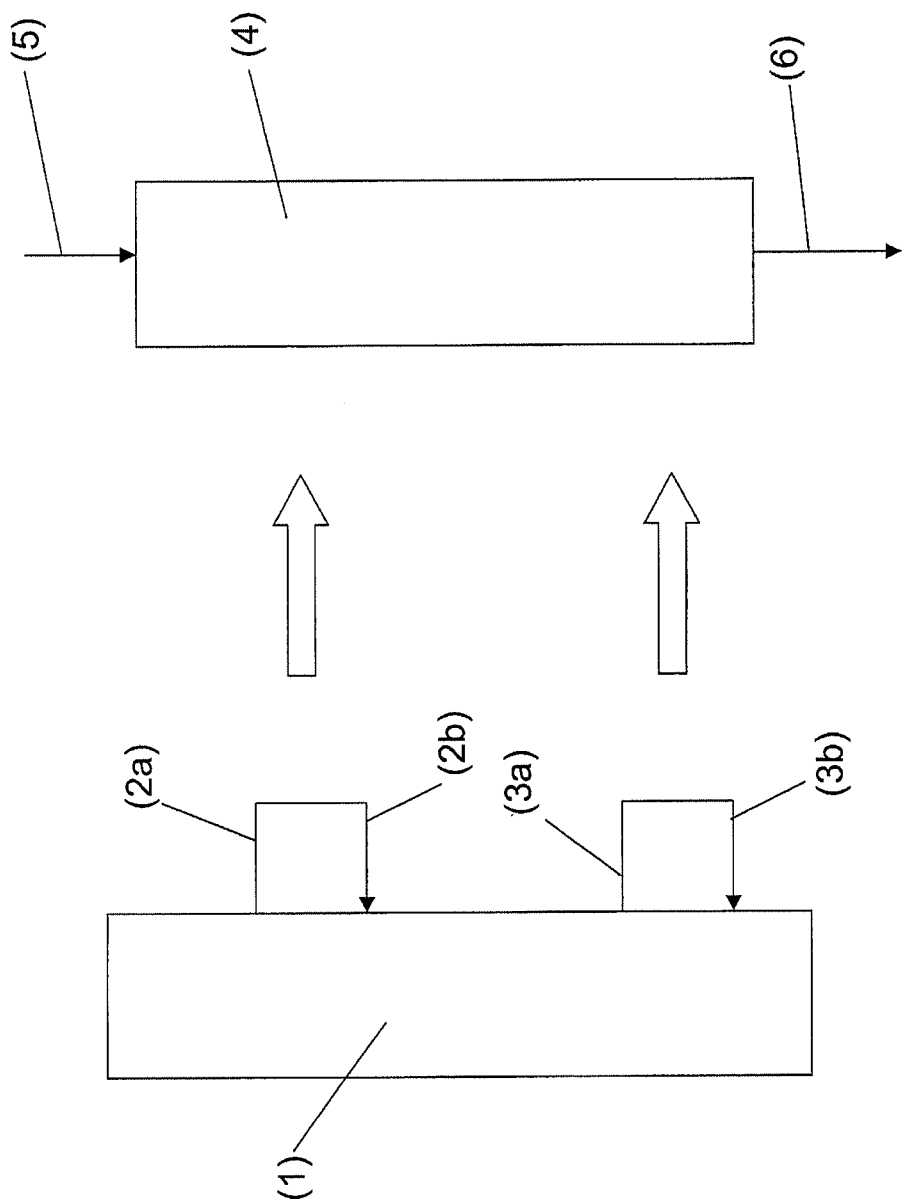
FIG. 2: An in-principle sketch of a plant according to the invention (as a newly built plant) and the method of the invention.

FIG. 2 shows a DCE plant (here a direct chlorination plant) (1). DCE vapor (2a) and hot liquid DCE (3a) are branched off from this. Heat is in each case recovered by condensation of the DCE vapor (2a) and by cooling of the liquid DCE (3a). The DCE condensate (2b) and the cooled DCE liquid (3b) are recirculated to the DCE plant (1). A multistage concentration apparatus (4) for aqueous alkali is heated by means of the heat obtained. In the example shown, this is not shown in detail but instead a block diagram of a multistage plant is shown. Aqueous sodium hydroxide (5) having a concentration of 30 about 30% by weight is introduced into this. The aqueous sodium hydroxide originates from a chloralkali electrolysis. In the multistage concentration apparatus (4), the aqueous sodium hydroxide (5) is concentrated by evaporation of water and leaves this apparatus (4) as aqueous sodium hydroxide (6) having a concentration of 50% by weight or more. Not shown in this in-principle sketch is that part of the heat required for heating the first stage of the multistage concentration apparatus (4) originates from waste heat obtained in further stages of the multistage concentration apparatus (4). The 5 apparatus depicted in FIG. 2 can preferably be realized in the construction of new DCE plants which are coupled with chloralkali plants.

Figure 3:
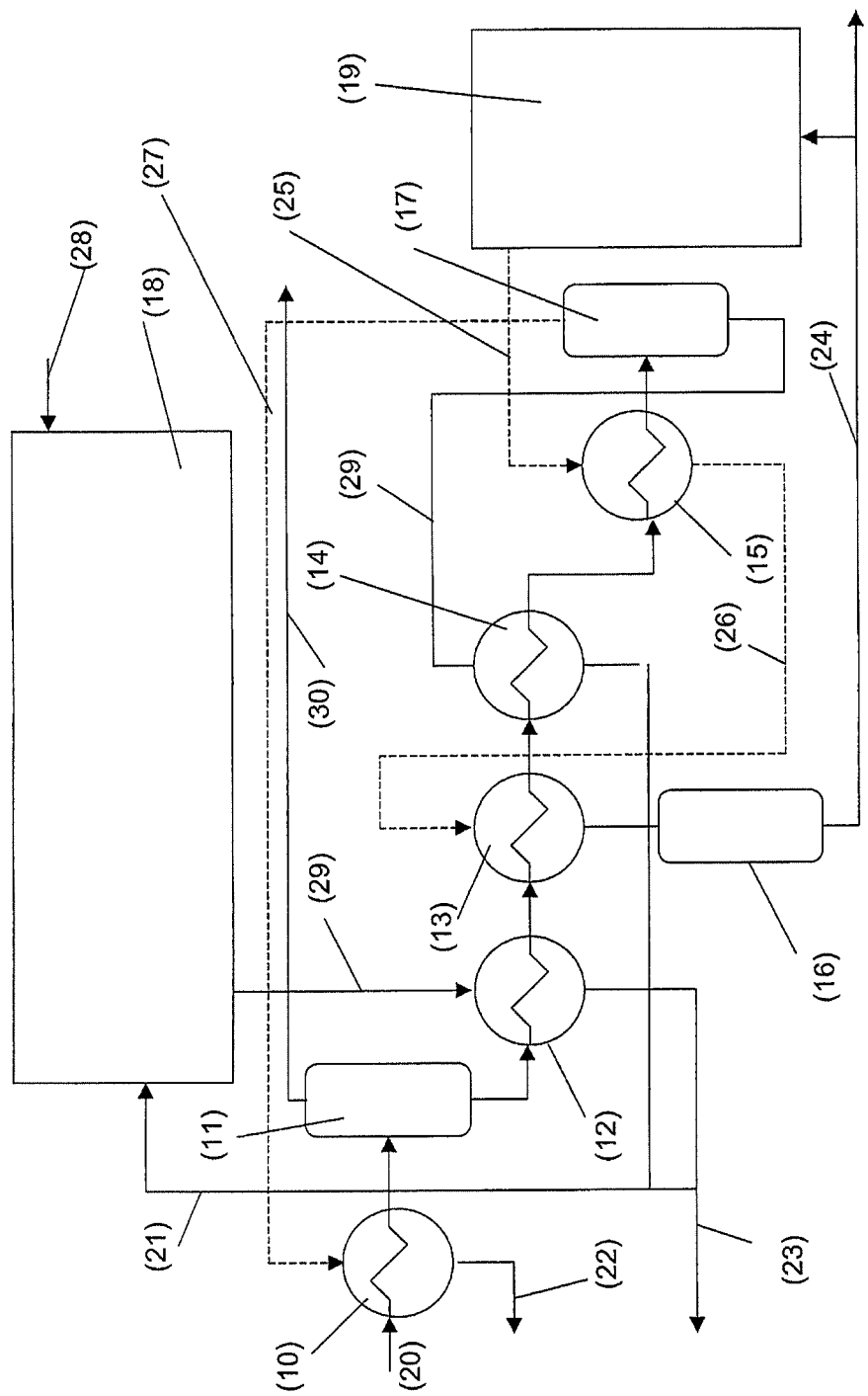
FIG. 3: A detailed sketch of a two-stage variant of the method of the invention and a plant for carrying it out (according to the principle of FIG. 1).

FIG. 3 describes a multistage apparatus for concentrating aqueous alkali. This apparatus can preferably be used for retrofitting integrated plants comprising a DCE plant and a chloralkali electrolysis plant, in which a conventional concentration apparatus for aqueous alkali is already present, as shown in FIG. 1. The multistage apparatus comprises an existing DCE plant (19), an existing conventional concentration apparatus (18) for aqueous alkali and a retrofitted multistage concentration apparatus for aqueous alkali. The conventional concentration apparatus (18) is operated using mainly high-pressure hot steam (28).

The retrofitted concentration apparatus shown in FIG. 3 comprises two concentration units. The first concentration unit is formed by a plate heat exchanger (10) and a phase separator (11) which is heated by steam (27) from the second concentration unit. The second concentration unit likewise comprises a plate heat exchanger (15) and a phase separator (17). The plate heat exchanger (15) is heated by DCE vapor (25) originating from the DCE plant (19). Between the first and second concentration units, there is a heating unit for the alkali concentrate which comprises three plate heat exchangers (12, 13, 14) connected in series. Heat exchanger (12) is heated by hot steam (29) originating from the conventional concentration apparatus (18). After passing through the heat exchanger (12), the cooled condensate (23) is discharged from the plant. Heat exchanger (13) is heated by the condensate (26) from the DCE vapor (25) which is obtained in heat exchanger (15). After passing through the heat exchanger (13), the cooled condensate is introduced into the collection vessel (16) and is, as DCE stream (24), from there recirculated to the DCE plant (19) or (partly) discharged from the plant. Heat exchanger (14) is heated by the concentrated hot alkali (29) originating from the phase separator (17). After passing through the heat exchanger (14), the cooled concentrated alkali (21) is introduced into the conventional concentration unit (18) in order to be concentrated further there.

The low concentration sodium hydroxide solution (20), e.g. 30% strength by weight from a chloralkali electrolysis plant (not shown in FIG. 3) is pumped into the plate heat exchanger (10), heated there and transferred into the phase separator (11). There, the water partly evaporates and is discharged as stream (30) from the plant, optionally after heat recovery by means of a heat exchanger (not shown). The preconcentrated alkali leaves the phase separator (11) and is heated further in the heating unit comprising three plate heat exchangers (12, 13, 14), then passes through heat exchanger (15) and is introduced into the phase separator (17). There, further water evaporates and the steam (27) is used for heating the heat exchanger (10) and then leaves the plant as cooled condensate (22). The concentrated alkali is pumped from the phase separator (17) and is, after passing through heat exchanger (14), introduced into the plant (18) for the purpose of further concentration.

Figure 4:
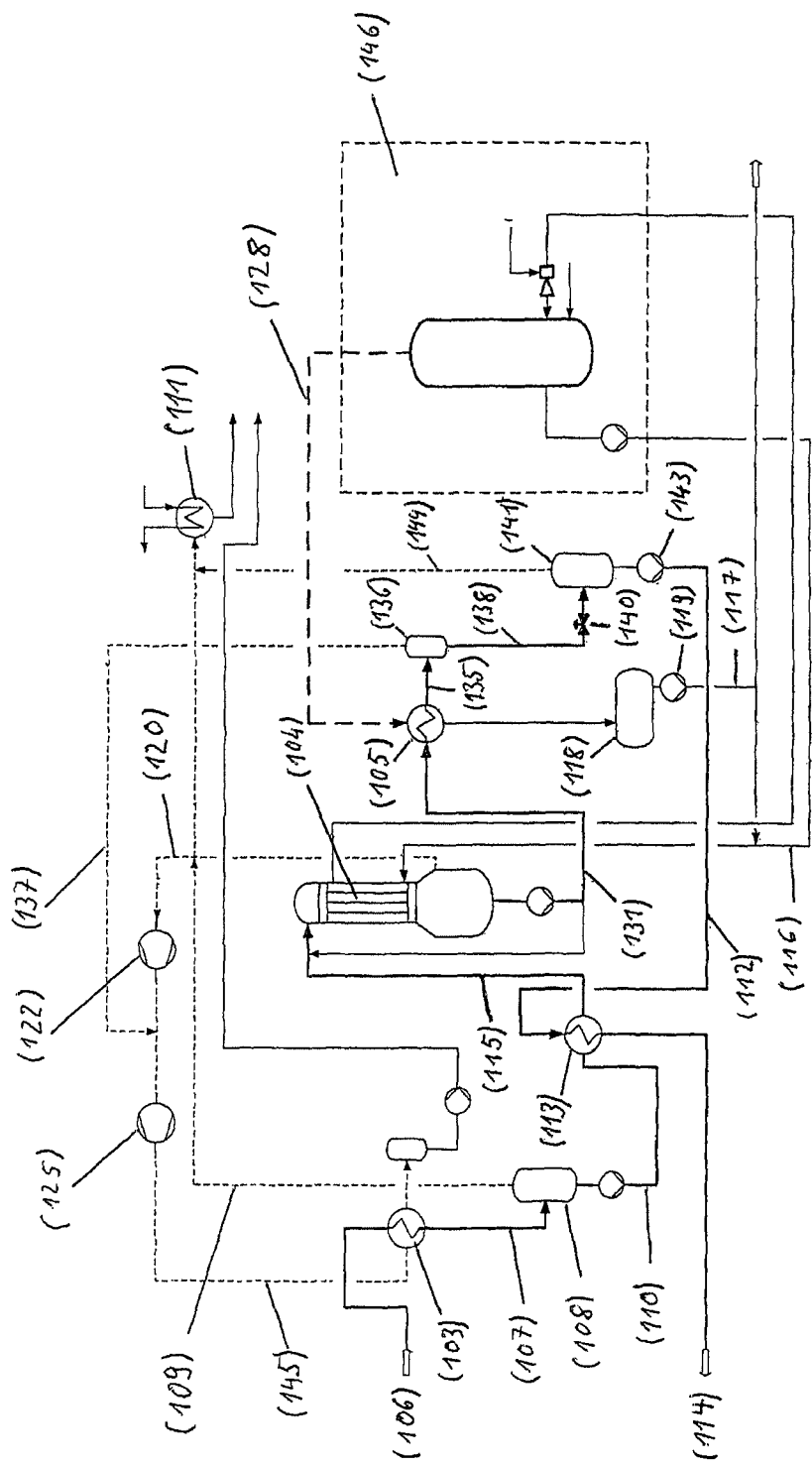
FIG. 4: A detailed sketch of a three-stage variant of the method of the invention and a plant for carrying it out (according to the principle of FIG. 2).

FIG. 4 describes a further apparatus for concentrating aqueous alkali. This apparatus can preferably be used in newly built plants or in plants in which no evaporation unit for aqueous alkali is yet present.

The apparatus depicted in FIG. 4 comprises three evaporation stages. The first evaporation stage comprises a heat exchanger (103) with downstream phase separator (108). The second evaporation stage comprises a falling film evaporator (104). The third evaporation stage comprises a further heat exchanger (105) with downstream phase separator (136). The second and third evaporation stages are heated by the usable part of the heat of reaction from the EDC plant, e.g. a direct chlorination apparatus. The first evaporation stage is heated by the heat obtained from compressed steam formed in the evaporation of sodium hydroxide solution.

Sodium hydroxide solution of low concentration, e.g. 30% strength by weight and coming from a chloralkali electrolysis plant (not shown in FIG. 4), enters, as stream (106), the heat exchanger (103) and is heated there and partly vaporized under reduced pressure. The heated sodium hydroxide solution is transferred as stream (107) into the phase separator (108) and separated there into steam (109) and preconcentrated sodium hydroxide solution (110). The steam (109) from phase separator (108) is condensed in the vacuum condenser (111) and the condensate is discharged from the plant.

The preconcentrated sodium hydroxide (110) is now heated further using the heat originating from the concentrated sodium hydroxide solution (112) end product (e.g. 50% strength by weight sodium hydroxide solution). For this purpose, the streams of sodium hydroxide solution (110, 112) are introduced into a heat exchanger (113), as a result of which the preconcentrated sodium hydroxide solution (110) is heated and the concentrated sodium hydroxide solution (112) is cooled. The cooled concentrated sodium hydroxide solution is discharged as stream (114) from the plant. The heated preconcentrated sodium hydroxide solution is introduced as stream (115) into a falling film evaporator (104) of the second evaporator unit. Falling film evaporator (104) is heated by liquid DCE (circulation stream (116)) originating from the DCE plant (146). Part of the condensed DCE (117) originating from the third evaporation stage is added from the collection vessel for condensed DCE (118) by means of DCE pump (119). This measure enables the sensible heat from the condensed DCE from the third evaporation stage likewise to be used. The steam (120) from the second evaporation stage (104) is compressed in a steam compression unit (122).

The third evaporation stage is operated by indirect heat exchange. DCE vapor (128) from the DCE plant (146), for example from a direct chlorination plant, is condensed in the heat exchanger (105). The condensation of the DCE vapor (128) heats and concentrates the preconcentrated sodium hydroxide solution (131) from the second evaporation stage (104) further in the heat exchanger (105). The concentrated sodium hydroxide solution (135) from heat exchanger (105) is freed of steam in the phase separator (136). Steam (137) from phase separator (136) is compressed in a steam compression unit (125). The concentrated sodium hydroxide solution (138) flows under the influence of gravity from phase separator (136) via a regulating valve (140) into phase separator (141). The concentrated sodium hydroxide solution (112) having a concentration of about 50% by weight of NaOH from phase separator (141) is pumped from the plant via heat exchanger (113) by means of the pump (143). The steam (144) separated off in the phase separator (141) is condensed in the vacuum condenser (111). The compressed steam (145) serves to heat the heat exchanger (103) of the first evaporation stage.

The invention claimed is:

1. A method for concentrating dilute aqueous alkali comprising utilizing heat of reaction from the formation of 1,2-dichloroethane, wherein the dilute aqueous alkali is concentrated in a plurality of stages, at least part of heat required for concentrating the dilute aqueous alkali originates from a plant for preparing 1,2-dichloroethane, and at least a further part of heat required for concentrating the dilute aqueous alkali originates from at least one higher stage of the plant for concentrating the aqueous alkali and is used for partial heating of a first stage of the plurality of stages, the method comprising the following steps:
producing a first aqueous alkali concentrate from a dilute aqueous alkali in a first concentration unit to which heat is supplied only by waste heat from one or more further concentration units,
further concentrating the first aqueous alkali concentrate to give a second aqueous alkali concentrate in a second concentration unit to which heat is supplied,
supplying at least part of the heat supplied to the second concentration unit in the form of heat originating from the plant for preparing 1,2-dichloroethane, and supplying at least a part of the heat supplied to the first concentration unit in the form of heat originating from the second concentration unit, and supplying heat to a heating unit located between the first and second concentration units to supply heat to the first alkali concentrate, at least part of the heat supplied to the heating unit being heat originating from at least one of: the plant for preparing 1,2-dichloroethane, the second concentration unit, and/or from a plant for concentrating aqueous alkali associated with a plant for chloralkali electrolysis, wherein the first and second concentration units each comprise a plate heat exchanger and a phase separator.

2. The method of claim 1, wherein the dilute aqueous alkali originates from a chloralkali electrolysis plant.

3. The method of claim 1, wherein the heating unit for the first aqueous alkali concentrate comprises from one to three heat exchangers connected in series.

4. The method of claim 1, wherein the method further comprises operating in three stages, comprising the following steps:

concentrating the second aqueous alkali concentrate to give a third aqueous alkali concentrate in a third concentration unit to which heat is supplied, providing at least part of the heat supplied to the second and third concentration units in the form of heat originating from the plant for preparing 1,2-dichloroethane, and providing at least part of the heat supplied to the first concentration unit in the form of heat originating from the second and third concentration units.

5. The method of claim 1, wherein the first concentration unit comprises one or more heat exchangers or evaporators connected in series, where at least 50% of the heat supplied to the first concentration unit originates from downstream concentration unit(s) and the heat is recovered therefrom by the use of heat exchangers, and/or from recompressed steam obtained in the operation of the downstream concentration unit(s).

6. The method of claim 1, wherein the second concentration unit comprises at least one falling film evaporator, where at least 50% of heat supplied to the second concentration unit is obtained from a 1,2-dichloroethane circulation stream originating from the plant for preparing 1,2-dichloroethane.

7. The method of claim 4, wherein the third concentration unit comprises at least one of a heat exchange or evaporator, where at least 50% of heat supplied to the third concentration unit is obtained from 1,2-dichloroethane vapor originating from the plant for preparing 1,2-dichloroethane.

8. The method of claim 7, wherein the vapor is condensed in the third concentration unit forming condensed 1,2-dichloroethane, a part of the condensed 1,2-dichloroethane from the third concentration unit is branched off for heating the second concentration unit and is combined with a 1,2-dichloroethane circulation stream coming directly from the plant for providing 1,2-dichloroethane.

9. An apparatus for concentrating aqueous alkali associated with a plant for preparing 1,2-dichloroethane, by the method of claim 1, comprising:

a first concentration unit for concentrating dilute aqueous alkali and for producing a first aqueous alkali concentrate, the first concentration unit being heated only by waste heat from one or more further concentration units;

a second concentration unit to which the first aqueous alkali concentrate is fed, for further concentrating the first aqueous alkali concentrate and producing a second aqueous alkali concentrate, the second concentration unit heated at least partially by heat originating from the plant for preparing 1,2-dichloroethane;

a heating unit for heating the first aqueous alkali concentrate, the heating unit located between the first and second concentration units; and a hot feed line coupled at an open end to a hot stream originating from at least one of the plant for preparing 1,2-dichloroethane, the second concentration unit, and/or from a plant for concentrating aqueous alkali associated with a plant for chloralkali electrolysis, and coupled at a second end with the heating unit, for supplying heat to the heating unit, wherein the first and second concentration units each comprise a plate heat exchanger and a phase separator.

10. The apparatus of claim 9, wherein the heating unit comprises three heat exchangers connected in series, a first heating unit heat exchanger heated by heat originating from the plant for preparing 1,2-dichloroethane, a second heating unit heat exchanger heated by heat originating from the second concentration unit, and a third heating unit heat exchanger heated by heat originating from the plant for concentrating aqueous alkali associated with the plant for chloralkali electrolysis.

11. The apparatus of claim 9, wherein the apparatus is retrofitted into an existing integrated plant comprising the plant for preparing 1,2-dichloroethane and the chloralkali electrolysis plant.

12. The apparatus of claim 9, further comprising:

a third concentration unit to which the second aqueous alkali concentrate is fed for concentrating the second aqueous alkali concentrate, to which heat is supplied at least in part in the form of heat originating from the plant for preparing 1,2-dichloroethane, and optionally the heating unit is formed by a heat exchanger unit coupled to the third concentration unit for recovering heat from the third concentration unit, the heat exchanger unit connected to the second concentration unit such that heat recovered by the heat exchanger unit is utilized for preheating the first aqueous alkali concentrate upstream of the second concentration unit.

13. The apparatus of claim 10, wherein the heat originating from the plant for preparing 1,2-dichloroethane is heat from a condensate of a 1,2-dichloroethane vapor obtained in a heat exchanger of the second concentration unit.

14. The apparatus of claim 12, wherein the first concentration unit is heated by steam from a steam compression unit which compresses steam originating from the second concentration unit and optionally from further concentration units.

15. The apparatus of claim 10, wherein the heating unit, the first concentration unit, and the second concentration unit are spatially separated from one another.

16. An apparatus for concentrating aqueous alkali comprising:

a first concentration unit for concentrating dilute aqueous alkali and for producing a first aqueous alkali concentrate, the first concentration unit being heated only by waste heat from one or more further concentration units;

a second concentration unit to which the first aqueous alkali concentrate is fed, for further concentrating the first aqueous alkali concentrate and producing a second aqueous alkali concentrate, the second concentration unit heated at least partially by heat originating from a plant for preparing 1,2-dichloroethane;

a heating unit for heating the first aqueous alkali concentrate, the heating unit located between the first and second concentration units; and one or more hot feed lines supplying heat to the heating unit, each hot feed line coupled at an open end to a hot stream originating from at least one of the plant for preparing 1,2-dichloroethane, the second concentration unit, and/or from a plant for concentrating aqueous alkali associated with a plant for chloralkali electrolysis, and coupled at a second end to the heating unit, wherein the first concentration unit, the second concentration unit, and the heating unit are spatially separated from one another.

17. The apparatus of claim 16, wherein the heating unit comprises three heat exchangers connected in series, each heat exchanger being heated by a different source of heat.

18. The apparatus of claim 16, wherein the heating unit comprises at least three heat exchangers connected in series, at least a first heating unit heat exchanger being heated by heat originating from the plant for preparing 1,2-dichloroethane, at least a second heating unit heat exchanger being heated by heat originating from the second concentration unit, and at least a third heating unit heat exchanger being heated by heat originating from the plant for concentrating aqueous alkali associated with the plant for chloralkali electrolysis.

19. The apparatus of claim 18, wherein the heat originating from the plant for preparing 1,2-dichloroethane is heat from a condensate of a 1,2-dichloroethane vapor obtained in a heat exchanger of the second concentration unit and/or the heat originating from the second concentration unit is heat from concentrated hot alkali originating from a phase separator of the second concentration unit.

* * * * *